United States Patent [19]

Mandai et al.

[11] Patent Number: 5,272,136

[45] Date of Patent: Dec. 21, 1993

[54] 5-0-α-D-GLUCOPYRANOSYL-L-ASCORBIC ACID, AND ITS PREPARATION AND USES

[75] Inventors: Takahiko Mandai; Masaru Yoneyama; Shuzo Sakai, all of Okayama, Japan

[73] Assignee: Kabushiki Kaisha Hayashibara Seibutsu Kagaku Kenkyujo, Okayama, Japan

[21] Appl. No.: 54,249

[22] Filed: Apr. 30, 1993

Related U.S. Application Data

[62] Division of Ser. No. 964,037, Oct. 21, 1992.

[30] Foreign Application Priority Data

Oct. 12, 1991 [JP] Japan .................................. 3-336399

[51] Int. Cl.$^5$ .................. A61K 31/70; A61K 9/68; A23G 3/30; C12P 19/60
[52] U.S. Cl. .................................... 514/27; 424/48; 424/59; 424/62; 426/3; 426/72; 426/311; 426/541; 426/548; 426/654; 426/658; 435/75; 435/97; 435/201; 435/202
[58] Field of Search .................. 435/72, 75, 97, 201, 435/202; 536/4.1, 16.8, 16.9, 18.6; 424/48, 59, 62; 426/3, 72, 311, 541, 548, 654, 658; 514/27

[56] References Cited

U.S. PATENT DOCUMENTS

| | | | |
|---|---|---|---|
| 3,763,009 | 10/1973 | Suzuki et al. | 435/72 |
| 4,487,198 | 12/1984 | Miyake et al. | 435/95 |
| 5,137,723 | 8/1992 | Yamamoto et al. | 536/4.1 |

FOREIGN PATENT DOCUMENTS

| | | |
|---|---|---|
| 48-38158 | 11/1973 | Japan . |
| 58-5920 | 2/1983 | Japan . |
| 58-23799 | 2/1983 | Japan . |
| 198498 | 11/1983 | Japan . |
| 135992 | 6/1991 | Japan . |
| 139288 | 6/1991 | Japan . |

OTHER PUBLICATIONS

Nippon Eiyo Shokuryo Gakkaishi, Journal of Japanese Society of Nutrition and Food Science, vol. 43, 1990.
Inst. for Agricultural and Biological Sciences, Okayama Univ., Kurashiki, Japan; Miyake et al.: vol. 43, No. 5; 1971, "Enzymatic Formation of New L-Ascorbic Acid Glycosides".
Inst. for Agricultural and Biological Sciences, Okayama Univ., Kurshiki, Japan, Suzuki et al.; vol. 47, No. 6; 1973; "Biosynthesis of Ascorbic Acid Glucoside".

*Primary Examiner*—Herbert J. Lilling
*Attorney, Agent, or Firm*—Browdy and Neimark

[57] ABSTRACT

5-O-α-D-Glucopyranosyl-L-ascorbic acid is a novel derivative of L-ascorbic acid which has a direct reducing activity and a satisfiable stability, as well as being readily hydrolyzed in vivo to form L-ascorbic acid. The 5-O-α-D-glucopyranosyl-L-ascorbic acid is prepared by allowing a saccharide-transferring enzyme together with or without α-glucosidase to a solution containing an a-glucosyl saccharide and L-ascorbic acid, and suitably used in food products, agents of anti-susceptive diseases and cosmetics containing thereof.

11 Claims, No Drawings

5-O-α-D-GLUCOPYRANOSYL-L-ASCORBIC ACID, AND ITS PREPARATION AND USES

This is a division of application Ser. No. 07/964,037 filed Oct. 21, 1992.

BACKGROUND OF THE INVENTION

1. Field of the Invention

The present invention relates to a novel 5-O-α-D-glucopyranosyl-L-ascorbic acid and its biochemical synthesis, as well as to food products such as beverages, processed foods, tobaccos and cigarettes; agents of antisusceptive diseases such as preventive and/or therapeutic agents for susceptive diseases; and cosmetics such as skin-refining agents and skin-whitening agents.

2. Description of the Prior Art

L-Ascorbic acid, which has the chemical structure shown by the formula 1:

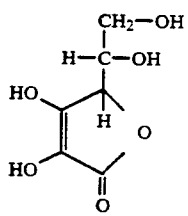

is not synthesized in vivo in human, monkey and guinea pig, therefore it is listed as an essential nutritive element, i.e. vitamin C.

L-Ascorbic acid takes part in some physiological activities in vivo; for example, in the hydroxylation of proline and lysine which are necessary to synthesize collagen as the main element of living connective tissues; the oxidation-reduction reaction of cytochrome C wherein $Fe^{+++}$ is reduced to $Fe^{++}$; and the immunopotentiation via the increase of leukocyte. These are because vitamin C plays a significant role in the maintenance and promotion of health in living body.

Scurvy has been known long as a condition due to deficiency of L-ascorbic acid, and is marked by weakness of the skin, petechial hemorrhage, ecchymosis, and hemorrhages in the gingiva and marrow. To prevent scurvy for the maintenance of health, a recommended daily administration (RDA) is established for L-ascorbic acid; in particular, 60 mg for adult male and 50 mg for adult female.

Nowadays the use of L-ascorbic acid is not limited to agents which enrich vitamin C as an essential nutritive element, but is extending in various applications. More particularly, because of the chemical structure and physiological activities, L-ascorbic acid is useful as a souring agent, reductant, antioxidant, bleaching agent and stabilizer in various chemical reagents, foods and beverages, pharmaceuticals for susceptive diseases such as preventive and remedy for viral diseases, bacterial diseases and malignant tumors; and further as a reductant, uv-absorbent and melanin-formation inhibitor in cosmetics including skin-refining agent and skin-whitening agent.

The major drawback of L-ascorbic acid is that it readily looses the physiological activities because of its poor stability and high susceptibility to oxidation.

To stabilize L-ascorbic acid, some saccharide derivatives of L-ascorbic acid have been proposed.

For example, a biochemical synthesis of L-ascorbic acid glucosides is disclosed in *Vitamin*, Vol.43, pp.205-209 (1971); ibid., Vol.47, pp.259-267 (1973); and Japanese Patent Publication No.38,158/73.

Because of the facts that (i) the glucosides are prepared by similar methods, (ii) "the formation of an ether bond at the primary alcohol group, which is located at the number six carbon atom in L-ascorbic acid, leads to the glucosides" as described in the Japanese Patent Publication, for example, on the 2nd column, lines 14-16, (iii) the saccharide-transfer reaction from maltose to an α-glucosyl group is responsible for the formation of glucosides, and (iv) the glucosides exhibit a direct reducing activity; the chemical structure of the glucosides would be shown by the formula 2:

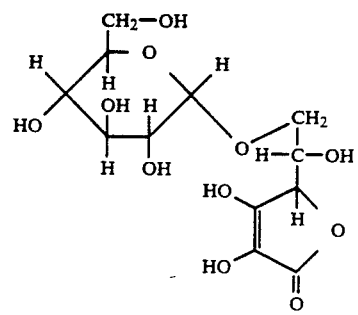

As obvious from the results in the Japanese Patent Publication, i.e. the table in Example 1, the stability of the glucosides is superior to that of L-ascorbic acid, but the level is not enough, and the glucosides can not sufficiently exert a physiological activity because they are substantially not assimilated by the digestive enzyme, and these render the commercialization of the glucosides difficult. Japanese Patent Laid-Open Nos.135,992/91 and 139,288/91 disclose that 2-O-α-D-glucopyranosyl-L-ascorbic acid as shown in formula 3 can be formed by a biochemical synthesis.

Formula 3:

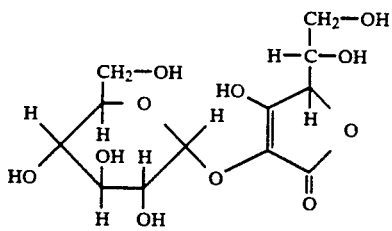

The derivative of L-ascorbic acid, however, has a drawback that it could not be used for uses wherein the inherent direct reducing activity of L-ascorbic acid is required.

While Japanese Patent Publication No.5,920/83 discloses an organic chemical process to synthesize saccharide derivatives of L-ascorbic acid.

These saccharide derivatives are, however, those wherein all the D-glucoses are bound in the β-fashion because up to 21 β-D-glucopyranosyl type derivatives of L-ascorbic acid including 2,3-di-O-(β-D-glucopyranosyl)-L-ascorbic acid are listed for explanation on the 7th column, line 6 to the 8th column, line 11.

Japanese Patent Laid-Open No.198,498/83 discloses an organic chemical process to synthesize saccharide derivatives of L-ascorbic acid which are also of β-glucosyl type.

Studies on the β-D-glucopyranosyl type derivatives of L-ascorbic acid confirmed that they hardly exhibit desired physiological activities in a living body, especially, in human.

Furthermore, conventional organic chemical processes have the drawbacks that they are inferior in economical efficiency because the reaction is very complicated and low in yield, as well as that the establishment of non-toxicity and safeness for the resultant derivatives is very difficult.

As described above, the proposals of saccharide derivatives of L-ascorbic acid in the prior art have proved unsatisfactory in view of stability, reducing activity, safeness, physiological activity and economical efficiency, and not been practiced hitherto.

It has been a great demand to realize a derivative of L-ascorbic acid which improves the drawbacks of conventional saccharide derivatives of L-ascorbic acid, as well as having a satisfiable stability, exhibiting a reducing activity, exerting the inherent physiological activity of L-ascorbic acid in vivo, and being used without fear of causing side effects.

SUMMARY OF THE INVENTION

The present invention was made to improve conventional drawbacks of L-ascorbic acid derivatives, more particularly, we studied a novel saccharide derivative of L-ascorbic acid which is obtainable by a biochemical process utilizing a saccharide-transfer reaction.

As a result, the present inventors found that a novel derivative of L-ascorbic acid, 5-O-α-D-glucopyranosyl-L-ascorbic acid, which has a satisfiable stability while exhibiting a direct reducing activity, and has an excellent physiological activity, as well as being readily hydrolyzed in vivo, and established the preparation and uses in food products, agents of anti-susceptive diseases and cosmetics. Thus, the present inventors accomplished this invention.

DETAILED DESCRIPTION OF THE INVENTION

Any method such as a biochemical process or an organic chemical process can be employed in the invention as long as it can prepare the present 5-O-α-D-glucopyranosyl-L-ascorbic acid.

In general, the present 5-O-α-D-glucopyranosyl-L-ascorbic acid is advantageously formed by a biochemical process wherein a saccharide-transferring enzyme is allowed to act on a solution containing an α-glucosyl saccharide and L-ascorbic acid in view of safeness and economical efficiency.

In the biochemical process, 5-O-α-D-glucopyranosyl-L-ascorbic acid is formed together with other substances such as 2-O-α-D-glucopyranosyl-L-ascorbic acid and 6-O-α-D-glucopyranosyl-L-ascorbic acid.

The wording "L-ascorbic acid" as referred to in the invention means L-ascorbates such as alkaline metal salts, alkaline earth metal salts and mixtures thereof, and should not be restricted to free L-ascorbic acid, as far as the present invention is feasible therewith.

Thus, if necessary, such as sodium L-ascorbate and calcium L-ascorbate are suitably used in the saccharide-transfer reaction, as well as free L-ascorbic acid.

The wordings "α-glycosyl-L-ascorbic acid", "2-O-α-D-glucopyranosyl-L-ascorbic acid", "5-O-α-D-Glucopyranosyl-L-ascorbic acid", and "6-O-α-D-glucopyranosyl-L-ascorbic acid" mean, in addition to those, those in free acid form, as far as the present invention is feasible therewith.

The α-glucosyl saccharides usable in the invention are those which permit a saccharide-transferring enzyme to form from L-ascorbic acid 5-O-α-D-glucopyranosyl-L-ascorbic acid. For example, maltooligosaccharides such as maltose, maltotriose, maltotetraose, maltopentaose, maltohexaose, maltoheptaose and maltooctaose; partial starch hydrolysates such as dextrin, cyclodextrin and amylose; and liquefied starch, gelatinized starch, and solubilized starch, are suitably chosen.

Consequently to facilitate the formation of 5-O-α-D-glucopyranosyl-L-ascorbic acid, one should choose an α-glucosyl saccharide which is susceptible to the saccharide-transferring enzyme to be used.

For example, when α-glucosidase (EC 3.2.1.20) is used as the saccharide-transferring enzyme, maltooligosaccharides such as maltose, maltotriose, maltotetraose, maltopentaose, maltohexaose, maltoheptaose and maltooctaose are suitable, as well as partial starch hydrolysates and dextrins with a DE (Dextrose Equivalent) of about 5–60. When cyclomaltodextrin glucanotransferase (EC 2.4.1.19) is used as the saccharide-transferring enzyme, partial starch hydrolysates such as gelatinized starches with a DE below 1 and dextrins with a DE up to 60 are suitable. When α-amylase (EC 3.2.1.1) is used as the saccharide-transferring enzyme, partial starch hydrolysates such as gelatinized starch with a DE below 1 and dextrins with a DE up to about 30 are suitable.

The concentration of L-ascorbic acid during the reaction is generally 1 w/w % or higher (the wording "w/w %" is abbreviated as "%" hereinafter, if specified otherwise), preferably, about 2–30%, while the concentration of an α-glucosyl saccharide is generally about 0.5- to 30-fold of L-ascorbic acid.

The saccharide-transferring enzymes usable in the invention are those which transfer one or several α-glucosyl groups at least to the number five carbon atom in L-ascorbic acid without decomposing it when allowed to act on a solution which contains L-ascorbic acid and an α-glucosyl saccharide having an adequate susceptivity to the enzyme.

For example, α-glucosidases derived from animals, plants and microorganisms such as those from mouse kidney, rat intestinal mucosa, dog small intestine, pig small intestine, rice seed, maize seed, and those from a culture which is obtainable by cultivating in a nutrient culture medium yeasts and bacteria of the genera Mucor, Penicillium and Saccharomyces; cyclomaltodextrin glucanotransferases from a culture of bacteria such as those of the genera Bacillus and Klebsiella; and α-amylase from a culture of bacteria such as those of the genus Bacillus are suitably chosen.

Such a saccharide-transferring enzyme should not necessarily be purified prior to its use, as long as it fulfills the above requirements. Generally, the present invention is feasible with a crude enzyme. If necessary, saccharide-transferring enzymes can be purified by conventional method, prior to its use.

Of course, commercialized saccharide-transferring enzymes can be used in the invention. The amount of a saccharide-transferring enzyme and reaction time are closely dependent each other. With an economical viewpoint, saccharide-transferring enzyme is used in an amount of which completes the reaction within about 3–80 hours.

Immobilized saccharide-transferring enzymes are favorably used batchwise and in continuous manner.

The reaction process according to the invention is usually carried out by adding a saccharide-transferring enzyme to a solution containing the above described L-ascorbic acid and an α-glucosyl saccharide, and keeping the mixture under conditions where the enzyme is substantially active; usually, at a pH in the range of about 3–9 and a temperature in the range of about 30°–80° C.

Since during the reaction, L-ascorbic acid tends to cause an oxidative decomposition, it is desirable to keep the mixture under anaerobic- or reducing-conditions which shield light as far as possible so that L-ascorbic acid is in its reducing form. The reaction is favorably carried out in the presence of such as thiourea and hydrogen sulfide, if necessary.

The desired substance can be advantageously obtained by incorporating an α-glucosyl saccharide and L-ascorbic acid in the culture of a growing microorganism which is capable of producing a saccharide-transferring enzyme.

The above-mentioned α-glucosyl-L-ascorbic acid, wherein one or more α-D-glucosyl groups bound at least to the alcohol group located at the number five carbon atom, has a structure wherein one or more glucosyl groups bound to the number five carbon atom in L-ascorbic acid via the α-1,4 fashion. Examples of such an α-glycosyl-L-ascorbic acid are 5-O-α-D-maltosyl-L-ascorbic acid, 5-O-α-D-maltotriosyl-L-ascorbic acid, 5-O-α-D-maltotetraosyl-L-ascorbic acid, 5-O-α-D-maltopentaosyl-L-ascorbic acid, 5-O-α-D-maltohexaosyl-L-ascorbic acid, and 5-O-α-D-maltoheptaosyl-L-ascorbic acid.

In the case of using a-glucosidase, the present 5-O-α-D-glucopyranosyl-L-ascorbic acid is usually formed together with 5-O-α-D-maltosyl-L-ascorbic acid and 5-O-α-D-maltotriosyl-L-ascorbic acid.

In the case of using either cyclomaltodextrin glucanotransferase or α-amylase, α-glycosyl-L-ascorbic acid with a higher α-D-glucosyl group are formed in mixture than in the case of using α-glucosidase. Dependently on the α-glucosyl saccharide, cyclomaltodextrin glucanotransferase yields α-D-glucosyl groups with a polymerization degree distributing in the range of 1–7, while α-amylase yields a slight narrower distribution.

Such a mixture can be partially hydrolyzed with either of α-amylase (EC 3.2.1.1), β-amylase (EC 3.2.1.2) and glucoamylase (EC 3.2.1.3) to reduce the polymerization degree of the α-D-glucosyl groups, if necessary.

For example, 5-O-α-D-maltosyl-L-ascorbic acid and higher polymers are hydrolyzed to accumulate 5-O-α-D-glucopyranosyl-L-ascorbic acid when subjected to glucoamylase. β-Amylase predominantly hydrolyzes 5-O-α-D-maltotriosyl-L-ascorbic acid and higher polymers to accumulate 5-O-α-D-glucopyranosyl-L-ascorbic acid and 5-O-α-D-maltosyl-L-ascorbic acid in mixture.

As described above, although a solution containing 5-O-α-D-glucopyranosyl-L-ascorbic acid formed by these methods usually contains 5-O-α-D-glucopyranosyl-L-ascorbic acid, 2-O-α-D-glucopyranosyl-L-ascorbic acid, 6-O-α-D-glucopyranosyl-L-ascorbic acid, and other intact L-ascorbic acid and α-glycosyl saccharides, the solution can be used intact as a product containing 5-O-α-D-glucopyranosyl-L-ascorbic acid.

The reaction mixture are usually heated to inactivate the remaining enzyme, filtered and concentrated into a syrupy product, and, if necessary the syrupy product is further dried and pulverized into a powdery product containing 5-O-α-D-glucopyranosyl-L-ascorbic acid.

When needed is a refined product with a high 5-O-α-D-glucopyranosyl-L-ascorbic acid content, such a reaction mixture is subjected to one or more separation methods wherein the difference between 5-O-α-D-glucopyranosyl-L-ascorbic acid and contaminants such as 2-O-α-D-glucopyranosyl-L-ascorbic acid, 6-O-α-D-glucopyranosyl-L-ascorbic acid, and remaining L-ascorbic acid, D-glucose and α-glucosyl saccharides in molecular weight and/or affinity is utilized; for example, membrane separation, gel filtration chromatography, column chromatography, high-performance liquid chromatography (HPLC) and ion exchange chromatography. Thus, the possible highest purity of 5-O-α-D-glucopyranosyl-L-ascorbic acid can be readily prepared.

In this case, the separated L-ascorbic acid and α-glucosyl saccharide can be favorably reused as a starting material in the saccharide-transfer reaction.

If necessary, after completion of the saccharide-transfer reaction but before separation by such as chromatography, the reaction mixture can be treated by one or more methods; for example, a method wherein the reaction mixture is heated and the insolubilized substances are removed by filtration; another method wherein the reaction mixture is treated, for example, with an activated charcoal to adsorb the proteinaceous substances for their removal; and one another method wherein the reaction mixture is demineralized with a cation exchange resin (H+-form), and treated with an anion exchange resin (OH−-form) to remove anions and salts by adsorption.

The 5-O-α-D-glucopyranosyl-L-ascorbic acid thus obtained has the following features:
(1) Although it exhibits a direct reducing activity, it is stabler than intact L-ascorbic acid.
(2) It is readily hydrolyzed by the in vivo enzyme into L-ascorbic acid and D-glucose to exert the inherent physiological activity of L-ascorbic acid.
(3) In the case of a product containing a saccharide such as an α-glucosyl saccharide, the product exerts the inherent activity of 5-O-α-D-glucopyranosyl-L-ascorbic acid and the saccharide exerts an excipient effect, a bulking effect and a sweetenining effect. In the case of a purified product obtained by removing the saccharide, though the excipient effect and bulking effect are reduced, the inherent activity of 5-O-α-D-glucopyranosyl-L-ascorbic acid is exerted with only a small amount.

Based on these features, 5-O-α-D-glucopyranosyl-L-ascorbic acid can be advantageously used as a quality-improving agent and uv-absorbing agent, as well as a vitamin P-enriched agent having a satisfiable stability and safeness, in food products; prophylactic- and therapeutic-agents for susceptive diseases such as virus diseases, bacterial diseases and malignant tumors; and cosmetics such as skin-refining agents and skin-whitening agents.

Since 5-O-α-D-glucopyranosyl-L-ascorbic acid having a relatively-high acid tolerance, light-tolerance and thermostability well harmonizes with substances having sour, saltiness, astringency, taste and bitterness, it can be advantageously used in a variety of general food products, cigarettes and tobaccos, for example, seasonings, Japanese-style confectioneries, western-style confectoneries, ice creams, sherbets, soft drinks, spreads, pastes, pickled products, bottled products, meat and fish meat products, processed marine products, egg and milk products, processed vegetable products, processed fruit products and processed cereal products.

5-O-α-D-Glucopyranosyl-L-ascorbic acid can be advantageously incorporated in feeds and pet foods for domestic animals including poutries, silkworms, bees and fishes as a vitamin P-enriched agent and taste-improving agent.

Also 5-O-α-D-glucopyranosyl-L-ascorbic acid can be favorably used as a substrate for assaying an enzyme which hydrolyzes α-glycosides and incorporated in foods, beverages, cigarette, tobacco, preventives and remedies for susceptive diseases, cosmetics including skin-refining agent and skin-whitening agent, for example, troche, candy in the form of tablet, cod-liver oil drop, soft drink containing vitamin complex, intubation nutrition, internal medicine, lipstick, hand cream, milky lotion, cream of sunscreen agent, dentifrice, cachou, gargle and lipstick.

The wording "susceptive diseases" as referred to in the invention means those which are prevented and/or treated with 5-O-α-D-glucopyranosyl-L-ascorbic acid; for example, viral diseases, bacterial diseases, traumatic diseases, immunopathies, diabetes, rheumatisms, and malignant tumors.

The shape and form of pharmaceuticals for susceptive diseases can be freely chosen to meet to their final use.

Examples of such a shape or form are liquid pharmaceuticals such as nebula, collyrium, collunarium, collutory and injection; paste pharmaceuticals such as ointment, cataplasm and cream; and solid pharmaceuticals such as powder, granule, capsule and tablet.

In the preparation of such a pharmaceutical, one or more ingredients, for example, remedy, biologically-active substance, antibiotic, adjuvant, filler, stabilizer, coloring agent and flavoring agent, can be suitably used in combination, if necessary.

The dose of the pharmaceuticals is adequately changed dependently on the 5-O-α-D-glucopyranosyl-L-ascorbic acid content, administration route and administration frequency; usually, in the range of about 0.001–100 g/day/adult as 5-O-α-D-glucopyranosyl-L-ascorbic acid content.

Cosmetics can be used similarly as in the pharmaceuticals.

5-O-α-D-Glucopyranosyl-L-ascorbic acid is incorporated in products by conventional method, for example, mixing, kneading, dissolving, melting, soaking, permeating, spreading, applying, coating, spraying, injecting, crystallizing and solidifying, before completion of their processing.

The 5-O-α-D-glucopyranosyl-L-ascorbic acid according to the present invention will be explained in detail by the following experiments.

EXPERIMENT 1

Formation and Isolation of Unknown Substance

Thirty parts by weight of dextrin (DE about 6) was dissolved in 40 parts by weight of water by heating, and the solution was added with 7 parts by weight of L-ascorbic acid under reducing conditions, further added with 250 units/g dextrin of cyclomaltodextrin glucanotransferase commercialized by Hayashibara Biochemical Laboratories, Inc., Okayama, Japan, and allowed to react for 40 hours while keeping the solution at pH 5.6 and 60° C.

High-performance liquid chromatography (HPLC) analysis of the reaction mixture revealed that about 65% of L-ascorbic acid was converted into α-glycosyl-L-ascorbic acid, said HPLC system and conditions comprising "LC-6A" column, a pump of Shimadzu Seisakusho Ltd., Kyoto, Japan; "Wakopak WB T-330", a column of Wako Pure Chemical Industries, Ltd., Osaka, Japan; "RI-7520", a differential refractometer of Eluma Optical Works Ltd., Tokyo, Japan; "875-UV", a uv-detector of Japan Spectroscopic Co., Ltd., Tokyo; 0.01 w/v % nitric acid as an eluate; and a flow rate of 0.5 ml/minute.

The reaction mixture was filtered with a UF-membrane to recover the remaining enzyme, and the resultant filtrate was adjusted to 50° C. and pH 5.0, added with 100 units/g dextrin of glucoamylase, and allowed to react for 6 hours.

The resultant mixture was heated to inactivate the remaining enzyme, decolored and filtered with an activated charcoal, and the resultant filtrate was concentrated, and subjected to column chromatography using a column packed with "DOWEX 50W-X4 (Ca++-form)", a strongly-acidic cation exchange resin commercialized by Dow Chemical Co., Midland, Mich., USA, in accordance with the method of column chromatography disclosed in Japanese Patent Laid-Open No.23,799/83. Thus, a fraction rich in 2-O-α-D-glucopyranosyl-L-ascorbic acid was recovered, and further subjected to a column packed with a cation exchange resin (H+-form) to effect demineralization and purification, and concentrated in vacuo to give a concentration of about 77%. The concentrate was placed in a crystallizer, added with a 2-O-α-D-glucopyranosyl-L-ascorbic acid seed crystal, adjusted to 40° C., gradually cooled to 20° C. over a period of 2 days under a gentle stirring condition, and fed to a bascket-type centrifuge to remove or separate a crystalline 2-O-α-D-glucopyranosyl-L-ascorbic acid. Thus, the first mother liquor was obtained in the yield of about 50% against the material L-ascorbic acid based on the weight of the dry solid (d.s.b.).

The first mother liquor was concentrated in vacuo similarly as above to effect recrystallization of 2-O-α-D-glucopyranosyl-L-ascorbic acid, and the resultant crystal was separated or removed to obtain the second mother liquor in the yield of about 25% against the material L-ascorbic acid, d.s.b.

HPLC analysis of the second mother liquor revealed that 2-O-α-D-glucopyranosyl-L-ascorbic acid and L-ascorbic acid were respectively detected at the positions of 18.7 and 29.7 minutes, while unknown peaks at the positions of 21.7 and 23.1 minutes, which were located between the above two positions, were detected and named as substances "X" and "Y" provisionally.

The contents of the substances X and Y in the second mother liquor were respectively about 10%, d.s.b., and each substance had about 65%, d.s.b., of 2-O-α-D-glucopyranosyl-L-ascorbic acid.

In order to isolate the substances X and Y from the second mother liquor, the coexisting large-amount of 2-O-α-D-glucopyranosyl-L-ascorbic acid should have been removed.

The present inventors studied the conditions to remove 2-O-α-D-glucopyranosyl-L-ascorbic acid, and found that 2-O-α-D-glucopyranosyl-L-ascorbic acid was more readily hydrolyzed than the substances X and Y under a relatively-high acidic- and temperature-condition. Thus, we removed 2-O-α-D-glucopyranosyl-L-ascorbic acid by using this hydrolysis.

The method was as follows: The second mother liquor was adjusted to give a concentration of 25%, adjusted to pH 1.7 by the addition of hydrochloric acid, and allowed to predominantly hydrolyze 2-O-α-D-glucopyranosyl-L-ascorbic acid at 100° C. Thereafter, the resultant solution was cooled and fed to a column packed with an anion exchange resin (OH$^-$-form) to adsorb the substances X and Y thereon, and the column was washed with water and fed with 0.5N hydrochloric acid to obtain a solution containing the substances X and Y.

The solution was subjected to an HPLC system wherein 0.01M $NaH_2PO_4$—$H_3PO_4$ (pH 2.0) was used as an eluate and a flow rate was 4.5 ml/minute, said HPLC system comprising "Model 510", a pump of Japan Waters Co., Tokyo, Japan; "D-ODS-5", a column of YMC Co., Ltd., Kyoto, Japan; and a uv-detector. Thereafter, a fraction rich in substance X or Y was recovered, and further deionized with "Micro acilyzer G1" equipped with "Cartridge AC-110", a deionizer commercialized by Asahi Chemical Industry, Co., Ltd., Tokyo, Japan, concentrated and lyophilized to obtain a powdery substance X or Y in the yield of about 20% against the content of the substance X or Y in the material mother liquor, d.s.b.

HPLC analysis of the substances X and Y revealed that the purities of the substances X and Y were about 98% and about 97% respectively.

EXPERIMENT 2

Physicochemical Property

The physicochemical properties of the high-purity substances X and Y in Experiment 1 will be described hereinafter.

(a) Elemental analysis: Calculated; C=42.6%, H=5.36%; Found (substance X); C=42.4%, H=5.37%; Found (substance Y); C=42.5%, H=5.37%; (for chemical formula $C_{12}H_{18}O_{11}$).

(b) Ratio of glucose and L-ascorbic acid: Calculated; Glucose L-ascorbic acid −1:1; Found (substance X); Glucose L-ascorbic acid =1.00:1.05; Found (substance Y); Glucose L-ascorbic acid =1.00:0.99.

Note The content of glucose was determined by the anthrone-sulfuric acid method, and the content of L-ascorbic acid was determined by the indophenol-xylene method.

(c) Ultraviolet absorption spectrum: The substances X and Y showed the maximum absorption spectra at 243 nm in a solution of pH 2.0, and at 265 nm in a solution of pH 7.0.

(d) Hydrolysis by enzyme of small intestinal membrane: In accordance with the method reported by Okada et al. in *Journal of Japanese Society of Nutrition and Food Science*, Vol.43, No.1 pp.23–29 (1990), the substances X and Y were subjected to the hydrolysis test using an enzyme of a small intestinal membrane, and it was revealed that the substance X was readily hydrolyzed but the substance Y was not substantially hydrolyzed.

(e) NMR spectrum: The nmr spectrum ($^{13}$C-NMR) of the substance X or Y showed 12 signals, and this meant all 12 carbons in each substance shifted differently. Each signal was assigned to α-D-glucopyranose and L-ascorbic acid as a standard substance, and the chemical shifts of the substances X and Y, as well as the standard substances, were as shown in Table 1.

TABLE 1

| L-Ascorbic acid | Substance X (A) | Substance Y (A) |
|---|---|---|
| C-1 | 174.0 | 176.8 | 176.7 |
| C-2 | 118.8 | 119.9 | 120.3 |
| C-3 | 156.4 | 161.4 | 160.4 |
| C-4 | 77.1 | 78.8 | 79.4 |
| C-5 | 69.9 | 77.2 | 70.8 |
| C-6 | 63.1 | 63.3 | 70.2 |

| α-D-Glucopyranose | Substance X (B) | Substance Y (B) |
|---|---|---|
| C-1 | 93.3 | 101.1 | 101.5 |
| C-2 | 72.8 | 75.1 | 74.9 |
| C-3 | 74.2 | 75.7 | 75.9 |
| C-4 | 70.9 | 71.8 | 72.5 |
| C-5 | 72.9 | 74.3 | 74.3 |
| C-6 | 62.3 | 62.9 | 63.5 |

Note:
The symbol "A" means L-ascorbic acid residue and the symbol "B" means α-D-glucopyranose residue.

Based on the results in Table 1, it is determined that the substance X is a novel substance having the structure as shown in the formula 4, i.e. 5-O-α-D-glucopyranose-L-ascorbic acid; and the substance Y is a known substance having the structure as shown in formula 2, i.e. 6-O-α-D-glucopyranosyl-L-ascorbic acid.

Formula 4:

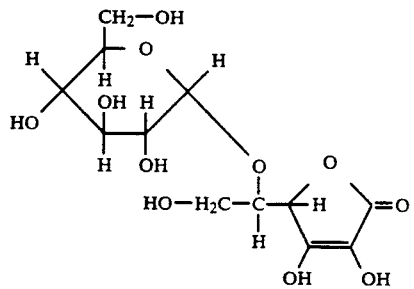

(f) Solubility in solvents: The substance X is readily soluble in water, 0.1N sodium hydroxide and 0.1M acetic acid; slightly soluble in methanol and ethanol; and insoluble in ether, benzene and chloroform.

(g) Coloring reaction: The substance X exhibits a reducing activity, and decolors 2,6-dichlorophenolindophenol. It turns green on the anthrone-sulfuric acid reaction.

(h) Stability: The stability of the substance X was compared with L-ascorbic acid as a control. Each specimen was adjusted to give a concentration of 70 μM and to pH 7.0 or pH 2.0, and the resultant each solution was placed in a cell for an absorption spectrophotometer. The cell was set to the absorption spectrophotometer and kept at 20° C., followed by determining at a prescribed time interval an absorbance at 265 nm with the solution of pH 7.0 and an absorbance at 243 nm with the solution of pH 2.0, and comparing the residual percentage (%) of each specimen. The results were as shown in Table 2.

TABLE 2

| pH | | Time (h) | | | | |
|---|---|---|---|---|---|---|
| | | 0 | 0.25 | 0.5 | 1.0 | 21.0 |
| 7.0 | 5GAsA | 100% | 58% | 35% | 16% | 6% |

TABLE 2-continued

| pH | | Time (h) | | | | |
|---|---|---|---|---|---|---|
| | | 0 | 0.25 | 0.5 | 1.0 | 21.0 |
| | AsA | 100% | 47% | 20% | 8% | 2% |
| 2.0 | 5GAsA | 100% | 99% | 98% | 90% | 50% |
| | Asa | 100% | 99% | 97% | 87% | 10% |

Note:
The symbol "5GAsA" means the present 5-O-α-D-glucopyranosyl-L-ascorbic acid and the symbol "AsA" means L-ascorbic acid as a control.

As evident from the results in table 2, it was revealed that the present 5-O-α-D-glucopyranosyl-L-ascorbic acid was stabler than L-ascorbic acid in an aqueous solution while exhibiting a direct reducing activity.

EXPERIMENT 3

A high-purity 5-O-α-D-glucopyranosyl-L-ascorbic acid, prepared by the method in Experiment 1, was orally administered to 7 week-old dd mice for acute toxicity test. As a result, no mouse died when administered with up to 5 g of the specimen, and a higher dose was difficult.

These confirmed that the specimen was extremely low in toxicity.

The following Examples A and B will illustrate the preparation of the present 5-O-α-D-glucopyranosyl-L-ascorbic acid and its uses respectively.

EXAMPLE A-1

Product Containing
5-O-α-D-glucopyranosyl-L-ascorbic acid

Nine parts by weight of dextrin (DE 10) was dissolved in 20 parts by weight of water by heating, and the solution was added with 3 parts by weight of L-ascorbic acid under reducing conditions, thereafter while keeping the solution at pH 5.5 and 65° C., added with 150 units/g dextrin of cyclomaltodextrin glucanotransferase, and allowed to react for 40 hours.

HPLC analysis of the reaction mixture revealed that about 50% of the L-ascorbic acid was converted into α-glycosyl-L-ascorbic acid.

Thereafter, the reaction mixture was heated to inactivate the remaining enzyme, adjusted to pH 4.5 and 55° C., added with 50 units/g dextrin of glucoamylase, and allowed to react for 24 hours.

The resultant mixture was heated to inactivate the remaining enzyme, decolored and filtered with an activated charcoal, and the filtrate was successively fed to a column packed with a cation exchange resin (H+- form) to remove minerals, and fed to a column packed with an anion exchange resin (OH−-form) to adsorb anionic substances thereon. Thereafter, the column packed with the anion exchange resin was washed with water to remove concomitants such as glucose and fed with 0.5N hydrochloric acid. The resultant effluent was concentrated and column chromatographed by using a column packed with a strongly-acidic cation exchange resin (H+-form), followed by recoverying a fraction rich in 2-O-α-D-glucopyranosyl-L-ascorbic acid.

The fraction was concentrated into an about 76% solution which was then added with 1% of a 2-O-α-D-glucopyranosyl-L-ascorbic acid seed crystal, heated to 40° C., gradually cooled to 25° C. over a period of 2 days under gently stirring conditions, and fed to a basket-type centrifuge to remove crystalline 2-O-α-D-glucopyranosyl-L-ascorbic acid. Thus, a syrupy mother liquor containing about 5% 5-O-α-D-glucopyranosyl-L-ascorbic acid was obtained in the yield of about 40% against the material L-ascorbic acid, d.s.b.

The product contains 5-O-α-D-glucopyranosyl-L-ascorbic acid together with a relatively-large amount of 2-O-α-D-glucopyranosyl-L-ascorbic acid and a relatively-small amount of 6-O-α-D-glucopyranosyl-L-ascorbic acid, and this renders it advantageously useful in food products, cosmetics and agents of anti-susceptive diseases as a stabilized saccharide derivative of L-ascorbic acid.

EXAMPLE A-2

Product Containing
5-O-α-D-glucopyranosyl-L-ascorbic acid

A mother liquor prepared by the method in Example A-1 was dried in vacuo and pulverized into a powder containing about 5% 5-O-α-D-glucopyranosyl-L-ascorbic acid, d.s.b.

Similarly as the product in Example A-1, the product can be advantageously used in food products, cosmetics and agents of anti-susceptive diseases as a stabilized saccharide derivative of L-ascorbic acid.

EXAMPLE A-3

Product Containing
5-O-α-D-glucopyranosyl-L-ascorbic acid

A second mother liquor prepared by the method in Experiment 1 was dried in vacuo and pulverized into a powder containing about 10% 5-O-α-D-glucopyranosyl-L-ascorbic acid, d.s.b.

Similarly as the product in Example A-1, the product can be advantageously used in food products, cosmetics and agents of anti-susceptive diseases as a stabilized saccharide derivative of L-ascorbic acid.

EXAMPLE A-4

5-O-α-D-Glucopyranosyl-L-ascorbic acid

A mother liquor prepared by the method in Example A-1 was fed to preparative HPLC in accordance with the method in Experiment 1, and the resultant fraction containing 5-O-α-D-glucopyranosyl-L-ascorbic acid was deionized, concentrated and pulverized to obtain a high-purity 5-O-α-D-glucopyranosyl-L-ascorbic acid in the yield of about 10% against the original content in the mother liquor.

The product has physicochemical properties as shown in Experiment 2, and can be advantageously used in food products, cosmetics and agents of anti-susceptive diseases.

EXAMPLE B-1

Chewing Gum

Twenty-five parts by weight of gum base and 20 parts by weight of a product containing 5-O-α-D-glucopyranosyl-L-ascorbic acid obtained by the method in Example A-2 were kneaded at 60° C. with a mixer, and the mixture was added with 50 parts by weight of "MABIT®", an anhydrous crystalline maltitol commercialized by Hayashibara Shoji Inc., Okayama, Japan, 1. 5 parts by weight of calcium phosphate and 0.1 part by weight of a β-cyclodextrin inclusion compound containing L-menthol, and further sufficiently mixed with a small amount of seasoning, rolled and cut to obtain the captioned product.

The product is a vitamin C-enriched, low-cariogenic and low-caloric chewing gum.

EXAMPLE B-2

"Gyuhi" (Starch Paste)

One part by weight of waxy rice starch was mixed with 1.2 parts by weight of water, and the mixture, while gelatinizing the starch by heating, was mixed to homogeneity with 1.5 parts by weight of sucrose, 0.7 parts by weight of "SUNMALT®", a crystalline β-maltose commercialized by Hayashibara Co., Ltd., Okayama, Japan, and 0.1 part by weight of a syrup containing 5-O-α-D-glucopyranosyl-L-ascorbic acid obtained by the method in Example A-1. The resultant mixture was in an usual manner formed and packed to obtain the captioned product.

The product is a vitamin C-enriched and Japanese-style confectionery like "kibi-dando" (millet dumpling) having a satisfiable biting property and taste. The product exhibits a relatively-long shelf-life because its retrogradation is effectively suppressed.

EXAMPLE B-3

Hard Candy

To 100 parts by weight of 55% sucrose solution was added 20 parts by weight of maltose while heating, and the mixture was concentrated in vacuo by heating, added with a syrup containing 5-O-α-D-glucopyranosyl-L-ascorbic acid obtained by the method in Example A-1, concentrated by heating to give a moisture content less than 2%. The resultant mixture was admixed with adequate amounts of a lemon flavor, color-imparting agent and citric acid, and formed in an usual manner into the captioned product.

The product is a relatively-high quality hard candy having a satisfiable biting property and taste, and the crystallization of sucrose is prevented.

EXAMPLE B-4

Chocolate

Forty parts by weight of cacao paste, 10 parts by weight of cacao butter, 50 parts by weight of anhydrous crystalline maltitol and one part by weight of a powder containing 5-O-α-D-glucopyranosyl-L-ascorbic acid obtained by the method in Example A-3 were mixed to homogeneity, and the mixture was fed to a refiner to reduce the particle size, transferred to a conche and kneaded at 50° C. for 2 days.

Before completion of the processing, 0.5 parts by weight of lecitin was added to the mixture and dispersed therein sufficiently. The resultant mixture was adjusted to 31° C. with a thermoregulator, and poured into a mold before the solidification of the butter, deaerated with a vibrator and passed through a tunnel kept at 10° C. for 20 minutes to effect solidification. The solidified product was removed from the mold and packed to obtain the captioned product.

The product is free of hygroscopicity and excellent in color, gloss and texture, and smoothly melts in the mouth to exhibit a mild taste and high-quality sweetness. The product is a vitamin C-enriched, low-cariogenic and low-caloric chocolate.

EXAMPLE B-5

Cream Filling

A cream filling was obtained by mixing to homogeneity in an usual manner 1,200 parts by weight of "FINETOSE®", a crystalline α-maltose commercialized by Hayashibara Co., Ltd., Okayama, Japan, 1,000 parts by weight of shortening, 10 parts by weight of a powder containing 5-O-α-D-glucopyranosyl-L-ascorbic acid obtained by the method in Example A-3, one part by weight of lecithin, one part by weight of lemon oil and one part by weight of vanilla oil.

The product is a vitamin C-enriched cream filling which is excellent in taste, flavor, melting and biting property, and the oxidation of the oils and fats are suppressed.

EXAMPLE B-6

Tablet

Twenty parts by weight of a high-purity 5-O-α-D-glucopyranosyl-L-ascorbic acid obtained by the method in Example A-4 was mixed to homogeneity with 13 parts by weight of crystalline β-maltose, 4 parts by weight of corn starch, one part by weight of rutin and 0.5 parts by weight of riboflavin, and the resultant mixture was tabletted to obtain the captioned product, 150 mg each.

The product is a stable and easily swallowable vitamin compound of vitamins C, P and $B_2$.

EXAMPLE B-7

Capsule

Ten parts by weight of calcium acetate monohydrate, 50 parts by weight of magnesium L-lactate trihydrate, 57 parts by weight of maltose, 20 parts by weight of a powder containing 5-O-α-D-glucopyranosyl-L-ascorbic acid obtained by the method in Example A-3, and 12 parts by weight of a γ-cyclodextrin inclusion compound containing 20% eicosapentaenoic acid were mixed to homogeneity, and the mixture was fed to a granulator, and then encapsulated in gelatin to obtain capsules, 150 mg each.

The product is favorably usable as a high-quality blood cholesterol lowering agent, immunopotentiation and skin-refining agent in preventive and remedy for susceptive diseases, as well as in food products directed to the maintenance and promotion of health.

EXAMPLE B-8

Ointment

One part by weight of sodium acetate trihydrate, 4 parts by weight of DL-calcium lactate and 10 parts by weight of glycerine were mixed to homogeneity, and the mixture was added to another mixture of 50 parts by weight of petrolatum, 10 parts by weight of vegetable wax, 10 parts by weight of lanolin, 14.5 parts by weight of sesame oil, one part by weight of a high-purity 5-O-α-D-glucopyranosyl-L-ascorbic acid obtained by the method in Example A-4 and 0.5 parts by weight of peppermint oil, and mixed to homogeneity to obtain an ointment.

The product is favorably usable- as a high-quality sunscreen agent, skin-refining agent, skin-whitening agent and promoter for healing injury and burn.

EXAMPLE B-9

Intubation Nutrition

A composition containing 20 parts by weight of crystalline α-maltose, 1.1 parts by weight of glycine, 0.18 parts by weight of sodium glutamate, 1.2 parts by weight of salt, one part by weight of citric acid, 0.4 parts by weight of calcium lactate, 0.1 part by weight of magnesium carbonate, and 0.1 part by weight of a powder containing 5-O-α-D-glucopyranosyl-L-ascorbic acid obtained by the method in Example A-3, 0.01 part by weight of thiamine, and 0.01 part by weight of riboflavin.

Twenty-four g aliquots of the composition were distributed to laminated aluminum small bags, and heat sealed to obtain the captioned product.

In use, one bag of the product is advantageously dissolved in about 300-500ml water, and administered to the nasal, stomach and intestine by the intubation feeding as an oral or parenteral intubation nutrition.

EXAMPLE B-10

Bath Liquid

A bath liquid was obtained by mixing 21 parts of DL-sodium lactate, 8 parts by weight of sodium pyruvate, 5 parts by weight of a powder containing 5-O-α-D-glucopyranosyl-L-ascorbic acid powder obtained by the method in Example A-2 and 40 parts by weight of ethanol with 26 parts by weight of refined water and appropriate amounts of coloring agent and flavoring agent.

The product is suitable for skin-refining agent and skin-whitening agent, which is diluted by 100-10,000-folds in bath water when in use. In this case, bath water is replaceable with cleansing liquid, astringent and moisture liquid.

EXAMPLE B-11

Milky Lotion

One half part by weight of polyoxyethylene behenyl ether, one part by weight of polyoxyethylene sorbitol tetraoleate, one part by weight of oil-soluble glyceryl monostearate, 0.5 parts by weight of pyruvic acid, 0.5 parts by weight of behenyl alcohol, one part by weight of avocado oil, one part by weight of a powder containing 5-O-α-D-glucopyranosyl-L-ascorbic acid obtained by the method in Example A-3 and appropriate amounts of vitamin E and antiseptic were dissolved in an usual manner by heating, and the solution was added with one part by weight of L-sodium lactate, 5 parts by weight of 1,3-butylene glycol, 0.1 part by weight of carboxyvinyl polymer and 85.3 parts by weight of refined water, emulsified with a homogenizer, added with an appropriate amount of a flavoring agent, and mixed by stirring to obtain the captioned product.

The product is favorably usable as a high-quality sunscreen agent, skin-refining agent and skin-whitening agent.

EFFECT OF THE INVENTION

As described above, the novel 5-O-α-D-glucopyranosyl-L-ascorbic acid according to the present invention has a direct reducing activity and a satisfiable stability, and it is readily hydrolyzed in vivo to exert the inherent activity of L-ascorbic acid.

Since the 5-O-α-D-glucopyranosyl-L-ascorbic acid is readily formed by a biochemical process wherein a saccharide-transferring enzyme together with or without glucoamylase is allowed to act on a solution containing an α-glucosyl saccharide and L-ascorbic acid, the present invention is economically satisfiable and industrially feasible.

The 5-O-α-D-glucopyranosyl-L-ascorbic acid having a direct reducing activity has a satisfiable stability and physiological activity, and these render it advantageously useful as a vitamin C-enriched agent, stabilizer, quality-improving agent, biologically active agent and uv-absorbing agent in food products such as beverages, processed food products, cigarettes and tobaccos, preventive and remedy for susceptive diseases, and cosmetics such as skin-refining agents, skin-whitening agents.

Accordingly, the present 5-O-α-D-glucopyranosyl-L-ascorbic acid has a wide applicability to a variety of fields, as well as having an industrial significance in the fields.

While there has been described what is at present considered to be the preferred embodiments of the invention, it will be understood the various modifications may be made therein, and it is intended to cover in the appended claims all such modifications as fall within the true spirits and scope of the invention.

We claim:

1. A process for preparing 5-O-α-D-glucopyranosyl-L-ascorbic acid, which comprises:
   (a) allowing a saccharide-transferring enzyme to act on a solution containing an α-glucosyl saccharide and L-ascorbic acid to form 5-O-α-D-glucopyranosyl-L-ascorbic acid; and
   (b) recoverying the resultant 5-O-α-D-glucopyranosyl-L-ascorbic acid.

2. The process of claim 1, wherein said saccharide-transferring enzyme in the step (a) is used together with glucoamylase (EC 3.2.1.3).

3. The process of claim 1, rein said saccharide-transferring enzyme is cyclodextrin glucanotransferase (EC 2.4.1.19).

4. The process of claim 1, wherein the concentration of said L-ascorbic acid is at least 1 w/w % based on the weight of the dry solid.

5. The process of claim 1, wherein the concentration of said α-glucosyl saccharide is about 0.5-30-fold of that of said L-ascorbic acid based on the weight of the dry solid.

6. The process of claim 1, wherein the pH and temperature in the step (a) are a pH in the range of about 3-9 and a temperature in the range of about 30°-80° C.

7. The process of claim 1, wherein said 5-O-α-D-glucopyranosyl-L-ascorbic acid in the step (a) is formed together with 2-O-α-D-glucopyranosyl-L-ascorbic acid and 6-O-α-D-glucopyranosyl-L-ascorbic acid.

8. The process of claim 1, wherein the step (a) is effected under anaerobic- or reducing-conditions which shield light.

9. A food product, which contains 5-O-α-D-glucopyranosyl-L-ascorbic acid.

10. An agent of anti-susceptive diseases, which contains an effective amount of 5-O-α-D-glucopyranosyl-L-ascorbic acid as an effective ingredient, wherein the dose of said agent is in the range of about 0.001-100g/day/adult of 5-O-α-D-glucopyranosyl-L-ascorbic acid.

11. A cosmetic which contains an effective amount of 5-O-α-D-glucopyranosyl-L-ascorbic acid as an effective ingredient, which is administered to a recipient at a dose of about 0.001-100g/day/adult of 5-O-α-D-glucopyranosyl-L-ascorbic acid.

* * * * *